(12) United States Patent
Matsumoto

(10) Patent No.: US 7,995,200 B2
(45) Date of Patent: Aug. 9, 2011

(54) ANALYZER

(75) Inventor: Daisuke Matsumoto, Kyoto (JP)

(73) Assignee: Arkray, Inc. (JP)

( * ) Notice: Subject to any disclaimer, the term of this patent is extended or adjusted under 35 U.S.C. 154(b) by 327 days.

(21) Appl. No.: 12/256,850

(22) Filed: Oct. 23, 2008

(65) Prior Publication Data

US 2009/0109433 A1 Apr. 30, 2009

(30) Foreign Application Priority Data

Oct. 26, 2007 (JP) ................. 2007-278462

(51) Int. Cl.
*G01N 1/10* (2006.01)

(52) U.S. Cl. .......... 356/244; 356/246; 356/39; 356/436; 422/105

(58) Field of Classification Search .......... 356/244, 356/246, 39, 436; 422/105, 100
See application file for complete search history.

(56) References Cited

U.S. PATENT DOCUMENTS 6,937,323 B2 * 8/2005 Worthington et al. .......... 356/73
7,061,594 B2 * 6/2006 Worthington et al. .......... 356/72
7,456,968 B2 * 11/2008 Potyrailo et al. .............. 356/436

FOREIGN PATENT DOCUMENTS

| JP | 2007-163344 | 6/2007 |
|----|-------------|--------|
| JP | 2007-170943 | 7/2007 |

* cited by examiner

*Primary Examiner* — L. G Lauchman
(74) *Attorney, Agent, or Firm* — Studebaker & Brackett PC; Donald R. Studebaker

(57) ABSTRACT

An analyzer in which optical measurement is performed with respect to a sample placed in optically transparent cells of an analysis tool includes a light source unit, a light-receiving unit, a tray on which the tool is placed, and a drive mechanism for driving the tray. The tray includes a holding section that holds the tool in a predetermined position. The drive mechanism reciprocates the tray between a first position where the tool placed on the tray is exposed to the outside of the analyzer and a second position where the tool is accommodated inside the analyzer. The light source unit is disposed so that emitted light is incident on a cell of the tool when the tray is located in the second position. The light-receiving unit is disposed so as to receive light transmitted through the cell when the tray is located in the second position.

4 Claims, 8 Drawing Sheets

FIG. 8A
FIG. 8B
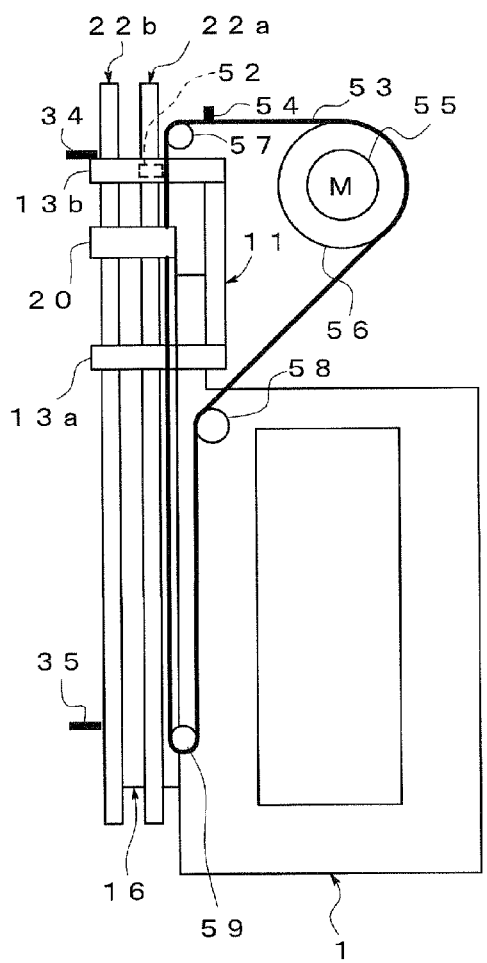
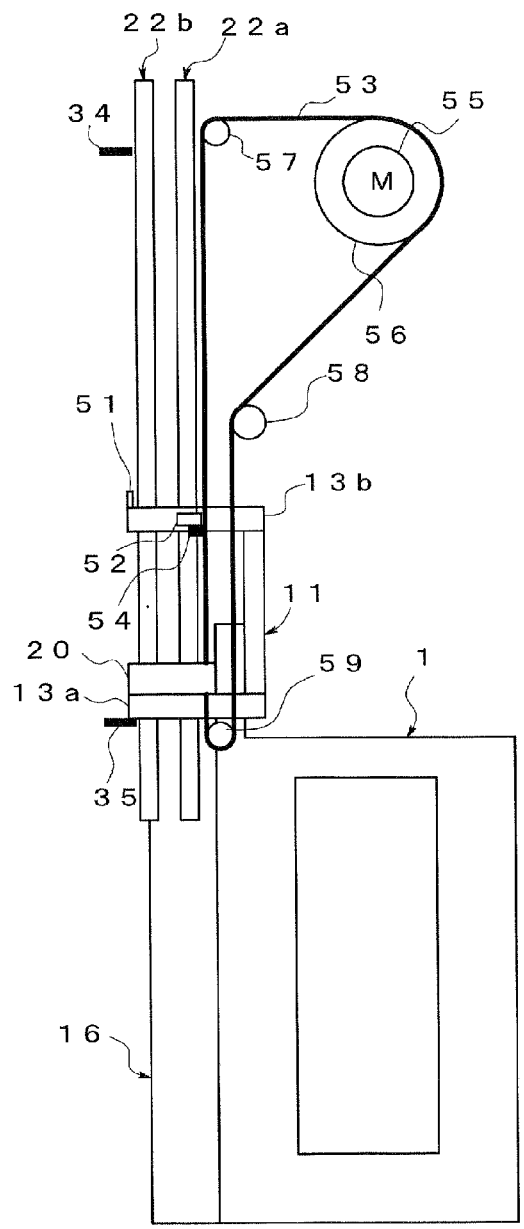

ANALYZER

CROSS-REFERENCE TO RELATED APPLICATIONS

This application claims priority to Japanese Patent Application No. 2007-278462. The entire disclosure of Japanese Patent Application No. 2007-278462 is hereby incorporated herein by reference.

BACKGROUND OF THE INVENTION

1. Field of the Invention

The present invention relates generally to analyzers used for analyzing components of samples.

2. Description of the Background Art

Conventionally, components of samples such as blood, interstitial fluid, urine, spinal fluid, and saliva are analyzed by, for example, absorbance measurement using an analysis tool called a biochip (or a microchip). The biochip is provided with minute analytical cells with diameters of around 1 mm or smaller and generally is configured with an optically transparent plate-like member bonded thereto (see, for example, JP 2007-163344 A and JP 2007-170943 A).

Specifically, the biochip is composed of an optically transparent substrate (transparent substrate) and an optically transparent cover for covering the transparent substrate. In the transparent substrate, minute concave portions to serve as cells and grooves to serve as minute channels for supplying a sample are formed. Furthermore, various reagents are placed in the respective cells of the biochip. When a sample is supplied into the cells through the channels, the reagents react with specific components in the sample and thereby colors are developed.

Furthermore, with respect to such a biochip, absorbance measurement is performed with an analyzer (see, for example, JP 2007-163344 A and JP 2007-170943 A). Specifically, the analyzer contains a light source unit that emits light and a light-receiving unit that receives light emitted from the light source unit. The biochip is inserted into the analyzer through an insertion opening thereof and is positioned so that a cell is located between the light source unit and the light-receiving unit.

Light emitted from the light source unit is incident on a cell. Part of the incident light is absorbed by the cell while the rest is transmitted therethrough to be received by the light-receiving unit. The analyzer calculates absorbance from the transmitted light that was received by the light-receiving unit. Furthermore, the concentration of a specific component contained in the sample is calculated from the absorbance. The concentration thus calculated is displayed on a display connected to the analyzer.

In order to improve the accuracy of absorbance calculation, it is necessary to optimize the positional relationship among the light source unit, the light-receiving unit, and a cell so that light emitted from the light source unit is incident on the cell properly and light transmitted through the cell is incident on the light-receiving unit properly. In this case, when the analyzer is configured so that the positional relationship among the three members are optimized by moving the light source unit and the light-receiving unit, the configuration of the analyzer is complicated and the cost increases.

Accordingly, analyzers employ the configuration in which the positional relationship among the three members are optimized by fixing the positions of the light source unit and the light-receiving unit and accurately placing a biochip in the predetermined position. For example, analyzers described in JP 2007-163344 A and JP 2007-170943 A each contain a member that comes into contact with one end of the microchip to position it. A user only needs to insert the microchip so that a part of the microchip comes into contact with the member.

However, the configuration in which the above-mentioned biochip is inserted through the insertion opening and is positioned by means of contact has a problem in that operational error made by the user tends to cause displacement since the cell is minute.

Furthermore, recently, a disk-shaped biochip has been proposed. In this biochip, a plurality of cells are arranged along an arc. When using a disk-shaped biochip, optical measurement can be performed with respect to each cell while the biochip is rotated, which allows efficient analysis to be performed. In such a disk-shaped biochip, however, it is difficult to position it by means of contact. Accordingly, the above-mentioned problem becomes further pronounced.

SUMMARY OF THE INVENTION

Hence, an object of the present invention is to solve the above-mentioned problem and to provide an analyzer that can prevent displacement of an analysis tool where a sample is placed and thereby can improve analytical precision regardless of the shape of the analysis tool.

In order to achieve the above-mentioned object, the analyzer of the present invention is an analyzer in which optical measurement is performed with respect to a sample placed in a cell of an analysis tool and is characterized by the following. The analyzer includes a light source unit that emits light for optical measurement, a light-receiving unit that receives light emitted from the light source unit and transmitted through the sample or reflected by the sample, a tray on which the analysis tool is placed, and a drive mechanism for driving the tray. The tray includes a holding section that holds, in a predetermined position, the analysis tool placed on the tray. The drive mechanism reciprocates the tray between a first position where the analysis tool placed on the tray is exposed to the outside of the analyzer and a second position where the analysis tool placed on the tray is accommodated inside the analyzer. The light source unit is disposed so that emitted light is incident on the cell of the analysis tool when the tray is located in the second position. The light-receiving unit is disposed so as to receive light transmitted through the cell when the tray is located in the second position.

The analyzer of the present invention provided with the aforementioned characteristics allows the analysis tool to be positioned accurately by merely placing the analysis tool on the tray ejected outside the analyzer. Furthermore, since the light source unit and the light-receiving unit are located in predetermined positions, light is incident properly on a cell and further transmitted light is received reliably.

Preferably, the analyzer of the present invention described above is in the mode in which the tray has an open part in a portion where the analysis tool is placed, the analyzer further includes a connector that is connected to the analysis tool and a supporting part that supports the analysis tool through the open part, the connector is connected to the analysis tool when the tray is located in the second position, the supporting part supports the analysis tool in an opposite position to the connector, and completion of connection by the connector and support by the supporting part releases holding of the analysis tool by the holding section.

According to the above-mentioned mode, after the tray is retracted into the analyzer, restraint of the analysis tool by the tray is released and the analysis tool is sandwiched between the connector and the supporting part. This results in further improvement in the accuracy of positioning with respect to a disk-shaped analysis tool. Moreover, in this case, the respective cells can be subjected to optical measurement sequentially, with the analysis tool being revolved. Thus efficiency of optical measurement with respect to the cells can be improved.

Furthermore, in the above-mentioned mode, it is preferable that all or part of a side wall of the open part be formed to conform to the outer shape of the analysis tool, the side wall of the open part have a convex section formed thereon that projects toward the inner side of the open part, and the portion formed to conform to the outer shape of the analysis tool and the convex section function as the holding section. In this case, the analysis tool can be positioned on the tray reliably with a simple configuration. Moreover, in this case, holding of the analysis tool by the holding section can be released by merely moving the tray downwards.

Furthermore, in the above-mentioned mode, it is preferable that the drive mechanism include a first slider and a second slider that slide along the direction in which the tray reciprocates, the first slider be connected to a portion of the tray located on a side of the second position so that the tray swings around a shaft perpendicular to the direction in which the tray slides and the normal direction of the analysis tool placed thereon, the second slider be joined to the tray through a cam mechanism, the cam mechanism be configured so that the tray swings around the shaft depending on the position of the second slider, and holding of the analysis tool by the holding section be released when the tray is swung by the cam mechanism to move the holding section of the tray.

In this case, the tray is retracted into the analyzer when the first slider slides and holding of the analysis tool by the tray is released when the second slider slides. Both the sliders slide in the same direction. Therefore, it is possible to retract the tray and release restraint of the analysis tool by the tray using only one power source (for example, an electric motor), and thus the cost of the analyzer can be reduced.

Furthermore, in this case, it is advantageous that the analyzer further includes an arm member for joining the connector and the second slider to each other, the arm member reciprocates the connector between a position where the connector is located away from the analysis tool and a position where it is connected to the analysis tool depending on the position of the second slider, and the connector is connected to the analysis tool after or before the cam mechanism moves the holding section of the tray. In this case, sliding of the second slider also can move the connector up and down. Accordingly, the connection between the connector and the analysis tool also can be achieved with one power source.

With the above-mentioned characteristics, the analyzer of the present invention can prevent the analysis tool where a sample is placed from being displaced, regardless of the shape of the analysis tool. As a result, the analyzer of the present invention can have improved analytical precision as compared to a conventional one.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 8A and 8B are diagrams showing an example of the power transmission mechanism of the embodiment.

BEST MODE FOR CARRYING OUT THE INVENTION

Embodiment

Figure 1:
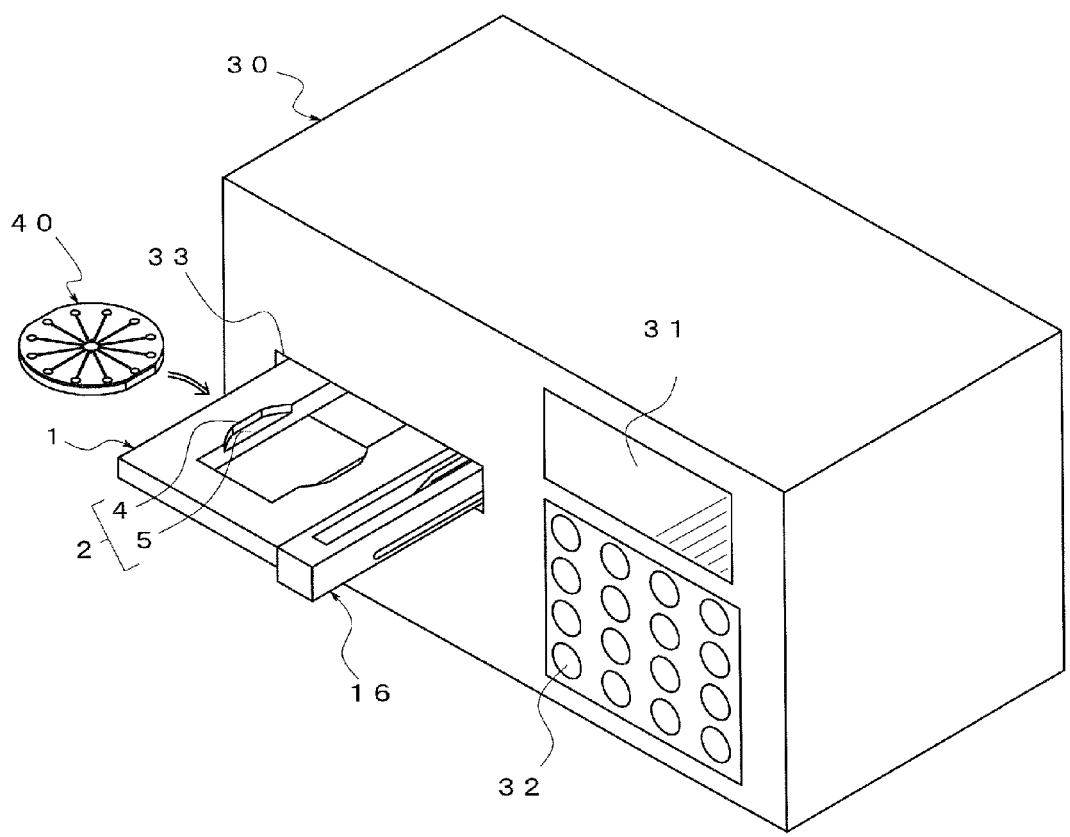
FIG. 1 is a perspective view showing the appearance of an analyzer according to an embodiment of the present invention.
Figure 2:
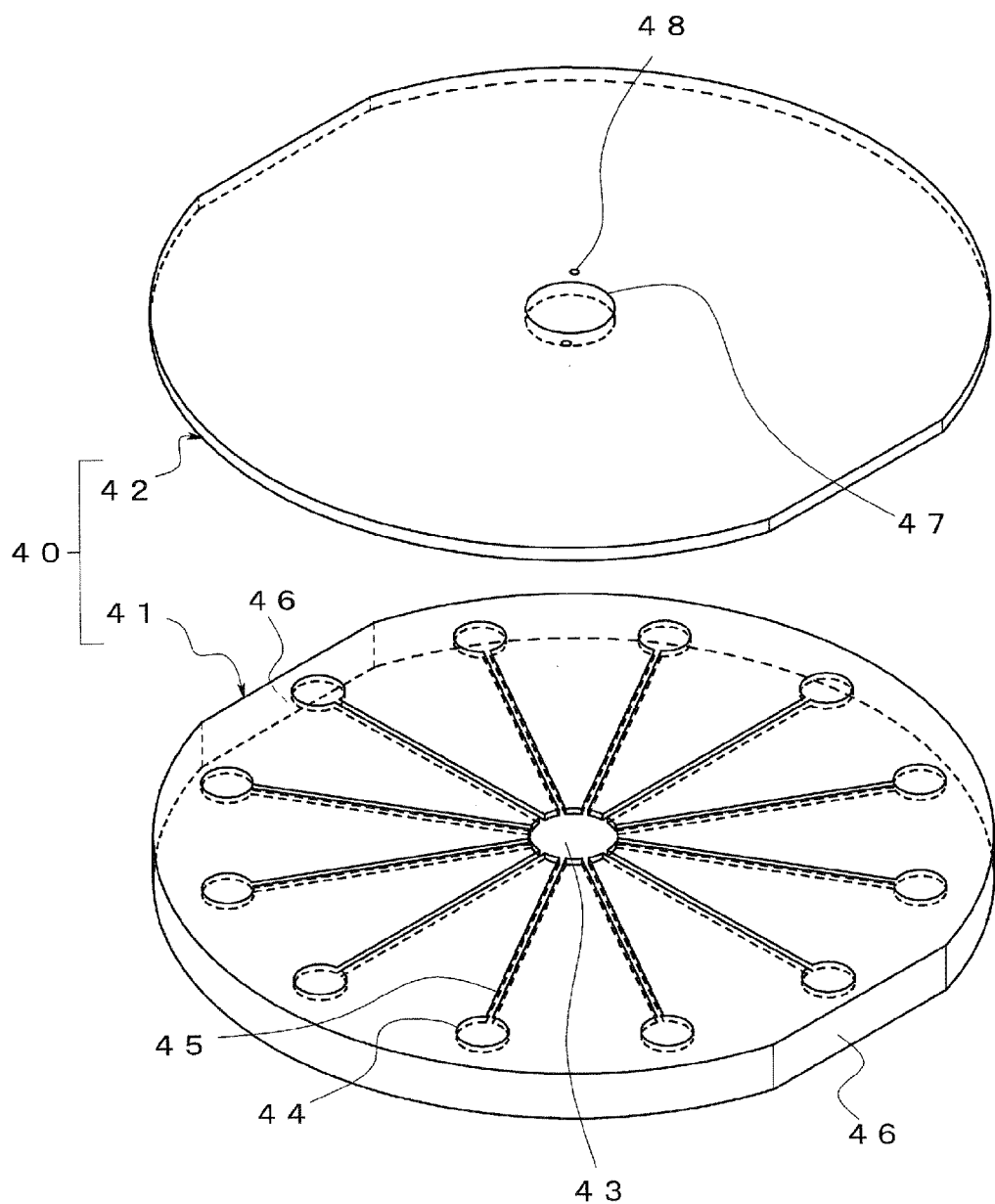
FIG. 2 is an exploded perspective view showing an example of an analysis tool that is used in the embodiment of the present invention.

Hereinafter, an analyzer according to an embodiment of the present invention is described with reference to FIGS. 1 to 8B. First, the overall configuration of the analyzer according to this embodiment and an analysis tool that is used in this embodiment are described with reference to FIGS. 1 and 2. FIG. 1 is a perspective view showing the appearance of the analyzer according to the embodiment of the present invention. FIG. 2 is an exploded perspective view showing an example of the analysis tool that is used in the embodiment of the present invention.

As shown in FIG. 1, the analyzer 30 according to this embodiment is an analyzer in which optical measurement is performed with respect to a sample and thereby components of the sample are analyzed. The sample is placed in optically transparent cells of an analysis tool 40, and the analyzer 30 performs optical measurement through the analysis tool 40 (see FIG. 2). The analysis tool 40 is one generally called a biochip.

As shown in FIG. 2, the analysis tool 40 includes an optically transparent substrate (transparent substrate) 41 and an optically transparent cover (transparent cover) 42 that covers the upper surface of the transparent substrate 41. The transparent substrate 41 is provided with a reservoir 43 where a sample is stored first, a plurality of cells 44 to be subjected to optical measurement, and a plurality of channels 45 connecting these. The reservoir 43, cells 44, and channels 45 are formed through formation of concave portions and grooves in the principal surface located on one side of the transparent substrate 41. Various reagents are placed in the cells 44 beforehand, although this is not shown.

Furthermore, in this embodiment, the analysis tool 40 has a plate shape with arcs formed in the periphery thereof. Specifically, the shape of the transparent substrate 41 viewed from the normal line is one obtained by cutting off two opposing portions of the circle (in other words, for example, a shape obtained by joining semicircles to two opposing sides of a rectangle). Accordingly, two planar sections 46 are formed on the side faces of the transparent substrate 41. These planar sections 46 are used for positioning the analysis tool 40 as described later. The outer shape of the transparent cover 42 is formed so as to match the outer shape of the transparent substrate 41.

Moreover, a plurality of cells 44 are arranged along the arcs of the outer shape of the analysis tool 40 and are arranged in a circle. One reservoir 43 is disposed in the center of the arranged cells 44, that is, in the center portion of the transparent substrate 41. In the center portion of the transparent cover 42, a supply port 47 for guiding a sample to the reservoir 43 is provided corresponding to the reservoir 43. The plurality of channels 45 are arranged radially and connect one reservoir 43 to the plurality of cells 44.

The sample supplied into the reservoir 43 is sent to the respective cells 44 through the respective channels 45. In each cell 44, a specific component in the sample reacts with the reagent placed beforehand and thereby a color is developed. Connecting holes 48 that are used for connecting the analysis tool 40 and the connector 23 described later are formed around the supply port 47 of the transparent cover 42.

In order to position such an analysis tool 40 accurately, as shown in FIG. 1, the analyzer 30 of this embodiment is different from a conventional analyzer and includes a tray 1 on which the analysis tool 40 is placed. The tray 1 is provided with holding sections 2 for holding the analysis tool 40 in a predetermined position. The configuration of the holding sections 2 is described later. Furthermore, the tray 1 reciprocates between a first position where the analysis tool 40 placed on the tray 1 is exposed to the outside of the analyzer 30 and a second position where the analysis tool 40 placed on the tray 1 is accommodated inside the analyzer 30 and optical measurement is performed.

Accordingly, this embodiment allows a user to position the analysis tool 40 accurately by merely placing the analysis tool 40 on the tray 1, which is different from conventional cases. Hereinafter, this embodiment is described in further details. In FIG. 1, numeral 31 indicates a display of the analyzer 30, 32 operation keys, and 33 a tray ejection opening. Furthermore, in this embodiment, the analysis tool is not limited to the analysis tool 40 shown in FIG. 2. That is, the analysis tool may be, for example, in the form of a rectangle whose outer shape is not in the form of an arc. The arrangement of the cells 44 may not be in a circular pattern. The cells 44 may be arranged linearly or in the form of matrix or may be arranged in random positions.

Figure 3:
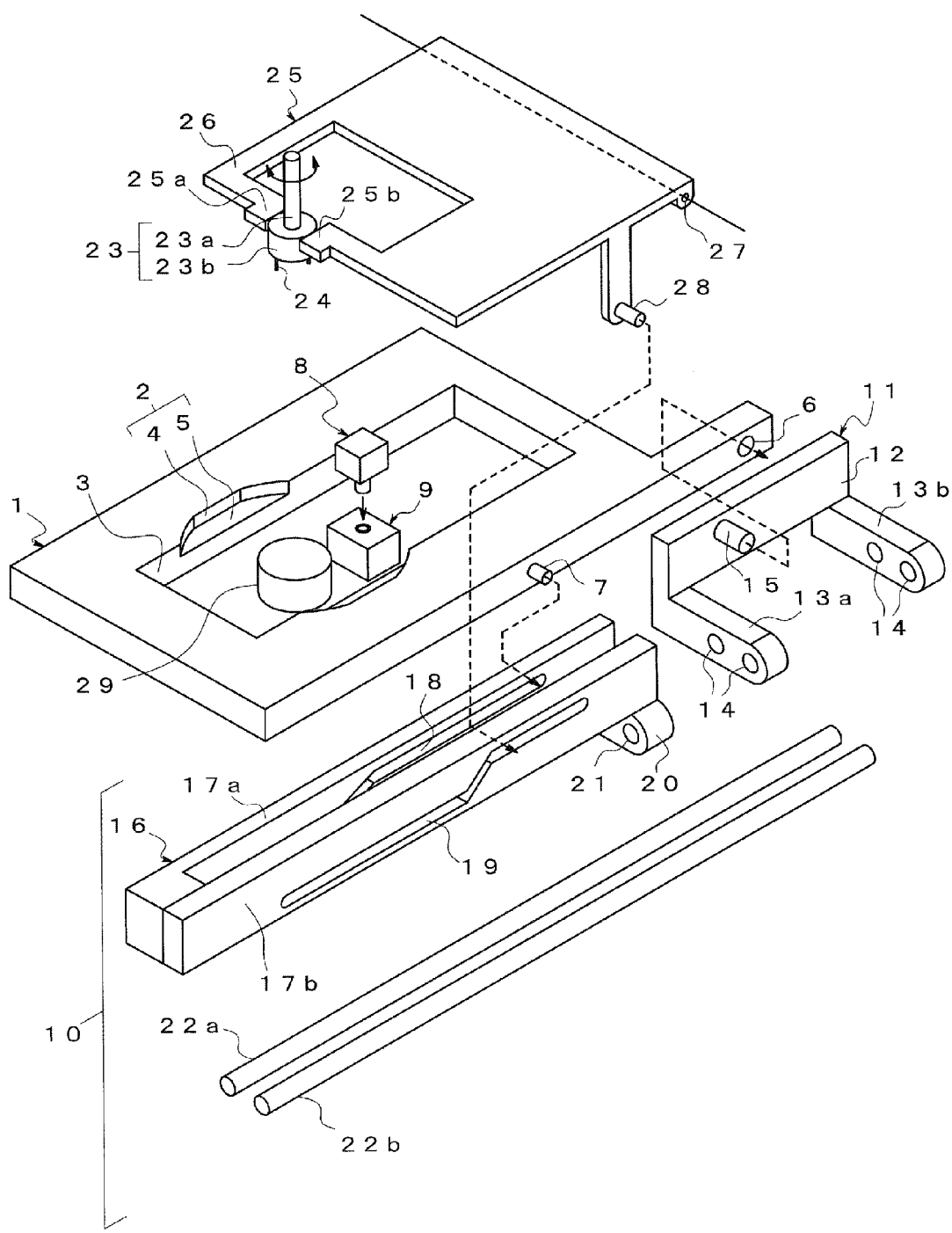
FIG. 3 is an exploded perspective view showing the main structural members of the analyzer according to the embodiment of the present invention.
Figure 4A:
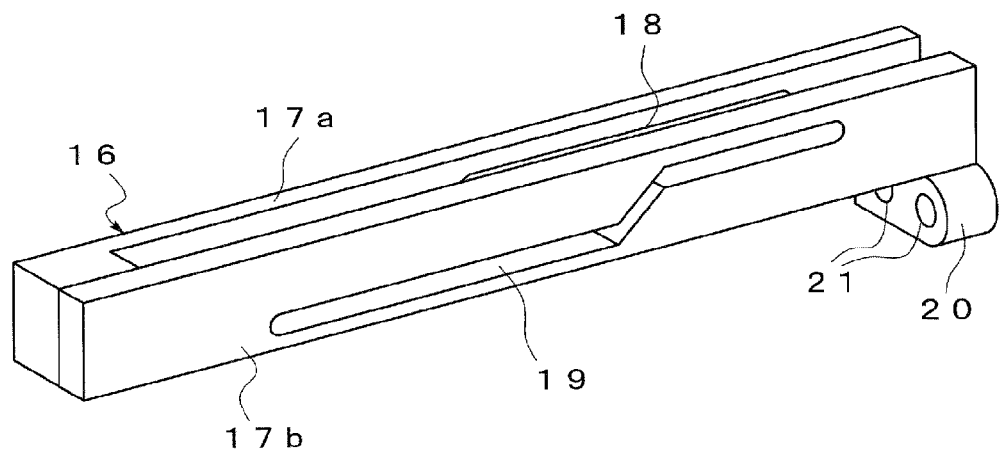
FIGS. 4A and 4B are perspective views showing a subslider illustrated in FIG. 3 and are different from each other in terms of projection angle.
Figure 4B:
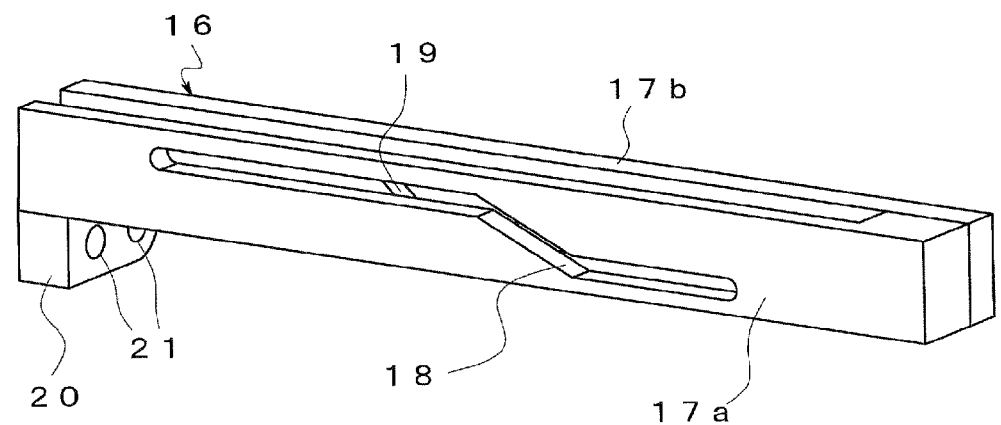
Figure 5:
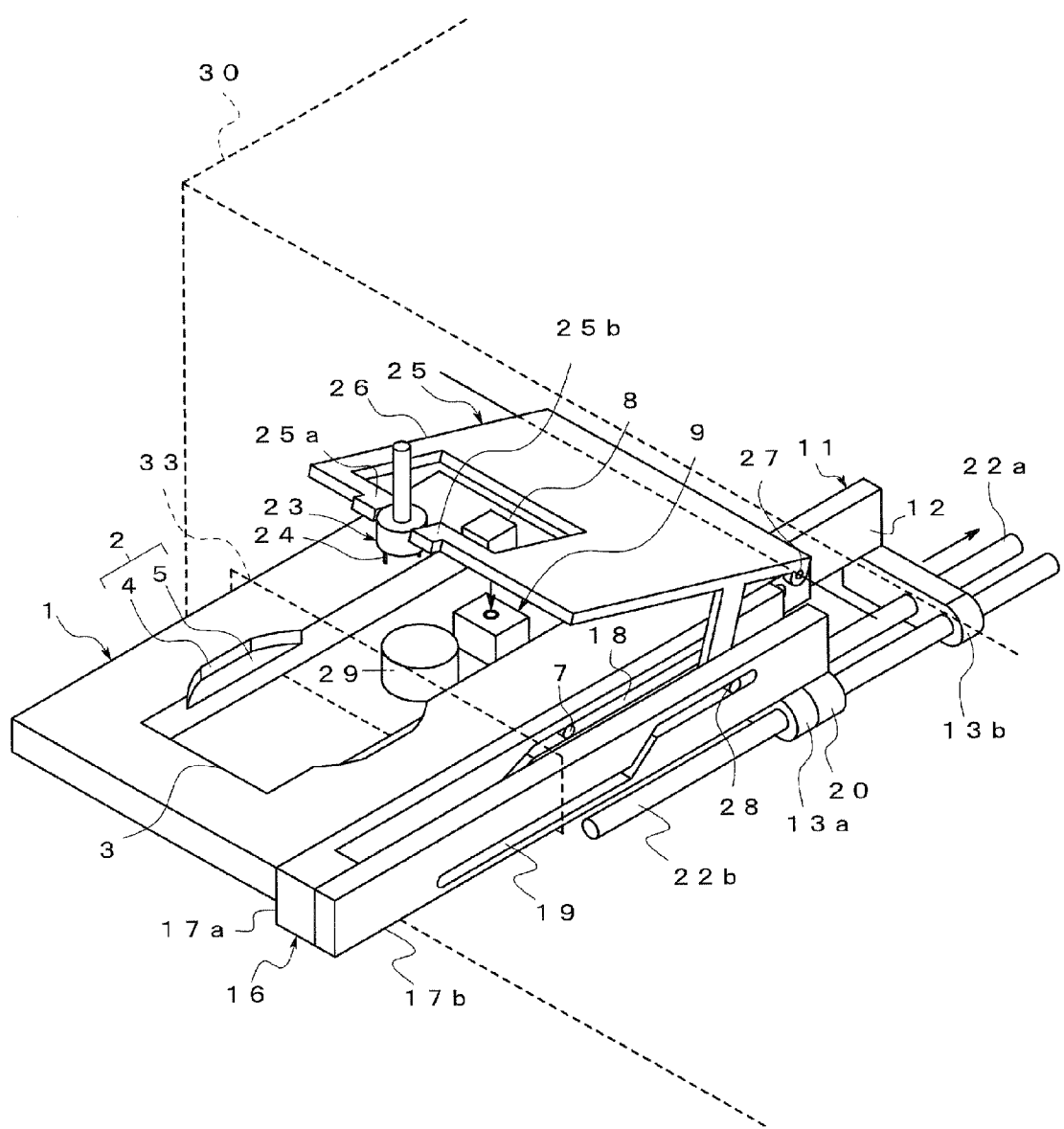
FIG. 5 is an assembly drawing of the structural members shown in FIG. 3 as well as FIGS. 4A and 4B and shows the state where the tray has being ejected outside the analyzer (first position).
Figure 6:
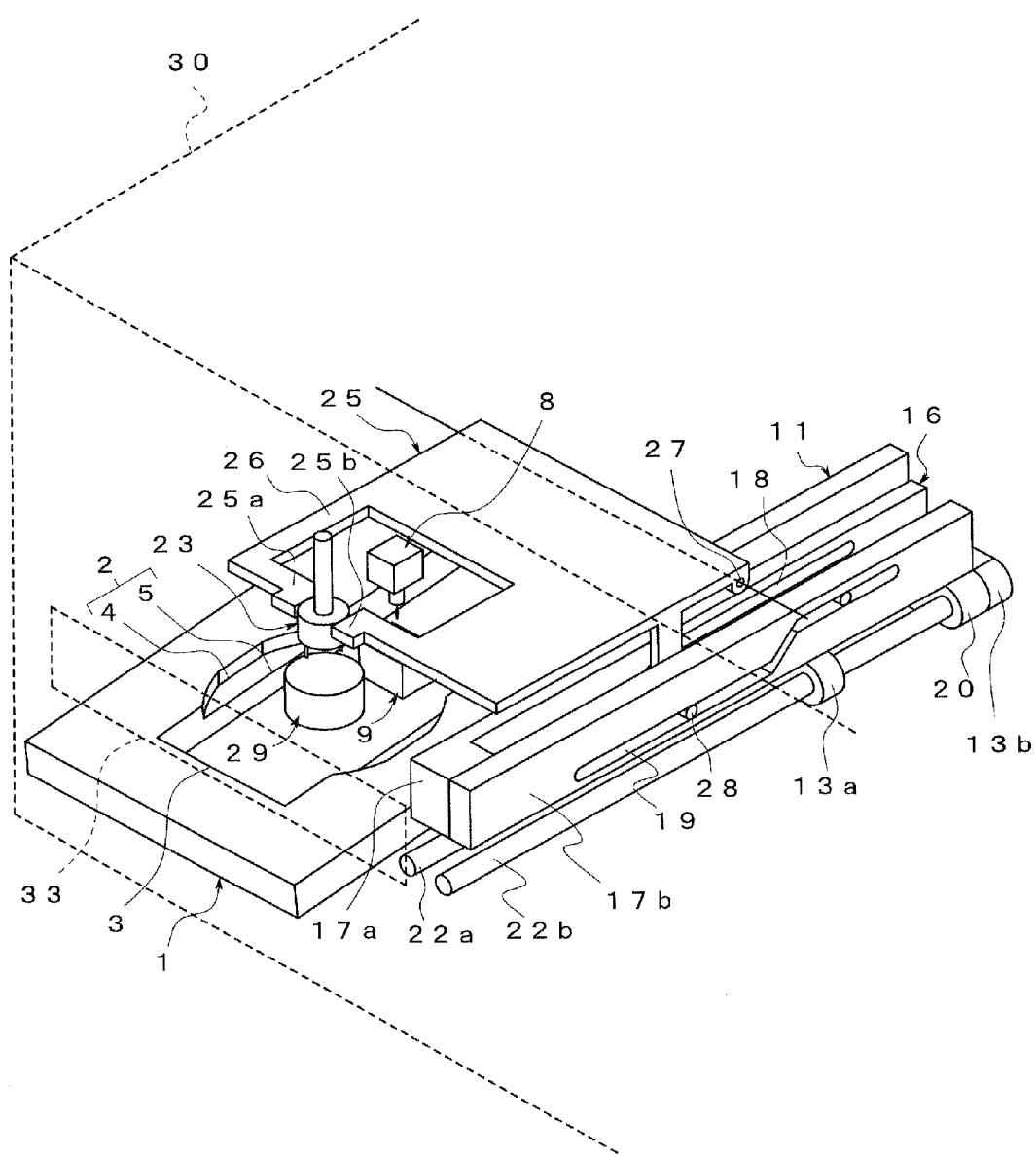
FIG. 6 is an assembly drawing of the structural members shown in FIG. 3 as well as FIGS. 4A and 4B and shows the state where the tray has been retracted inside the analyzer (second position).

The internal configuration of the analyzer according to this embodiment is described with reference to FIGS. 3 to 6. FIG. 3 is an exploded perspective view showing the main structural members of the analyzer according to the embodiment of the present invention. FIGS. 4A and 4B are perspective views showing a subslider illustrated in FIG. 3 and are different from each other in terms of projection angle. FIGS. 5 and 6 are assembly drawings of the structural members shown in FIG. 3 as well as FIGS. 4A and 4B. FIG. 5 shows the state where the tray has been ejected outside the analyzer (first position). FIG. 6 shows the state where the tray has been retracted inside the analyzer (second position).

As shown in FIG. 3, the analyzer of this embodiment includes the tray 1 that was described with reference to FIG. 1, a light source unit 8 that emits light for optical measurement, a light-receiving unit 9 that receives light (emitted light) emitted from the light source unit 8, and a drive mechanism 10. The drive mechanism 10 drives the tray 1 to reciprocate it between the first position (see FIG. 5) and the second position (see FIG. 6).

The light source unit 8 is disposed so that light (emitted light) emitted therefrom is incident on a cell 44 of the analysis tool 40 (see FIG. 2) when the tray 1 is located in the second position. The light-receiving unit 9 is disposed so as to receive light transmitted through the cell 44 when the tray 1 is located in the second position. In this embodiment, the light source unit 8 and the light-receiving unit 9 are fixed to a frame (see FIG. 7) of the analyzer. Since the light source unit 8 and the light-receiving unit 9 are located in predetermined positions, mere positioning of the analysis tool 40 reliably allows light to be incident on the cell 44 and transmitted light to be received.

In this embodiment, the light source unit 8 includes a light source such as a semiconductor laser or a light emitting diode and an optical system and emits light with a predetermined wavelength. The light-receiving unit 9 includes a light receiving element such as a photodiode or a phototransistor and outputs signals according to the amount or intensity of light received thereby.

In this embodiment, the tray 1 has an open part 3 in a portion where the analysis tool 40 is placed. Parts of the side walls of the open part 3 are formed to conform to the outer shape of the analysis tool 40 and serve as positioning sections 4. The side walls of the open part 3 have convex sections 5 formed thereon that project toward the inner side of the open part 3.

Specifically, the open part 3 is formed so that the shape of the opening is a rectangular shape with the direction of its long axis being the direction in which the tray 1 moves (or a similar shape thereto). Each positioning section 4 is obtained by allowing the shape of a portion of the side wall of each long side of the open part 3 to have a shape corresponding to those of a planar section 46 (see FIG. 2) of the analysis tool 40 and a portion surrounding the planar section 46. Furthermore, each convex section 5 is obtained by providing a step in the lower part of the positioning section 4.

Accordingly, when the planar sections 46 (see FIG. 2) of the analysis tool 40 conform to the positioning sections 4 of the tray 1 and the analysis tool 40 is supported by the convex sections 5, placement of the analysis tool 40 on the tray 1 and positioning thereof are completed. In this embodiment, the positioning sections 4 and the convex sections 5 function as the holding sections 2 described above, and therefore the analysis tool 40 can be positioned on the tray 1 reliably with a simple configuration. The open part 3 may be formed so that all the side walls thereof conform to the outer shape of the analysis tool 40. The configuration of the holding sections 2 is not limited to the mode described above.

In this embodiment, the drive mechanism 10 includes a main slider 11 and a subslider 16 (see FIGS. 4A and 4B). The main slider 11 and the subslider 16 slide along the direction in which the tray 1 reciprocates, using power transmitted from a power source. The power source is described later.

Specifically, the main slider 11 and the subslider 16 slide along two slide shafts 22a and 22b (see FIGS. 5 and 6). The slide shafts 22a and 22b are disposed in parallel with each other. Furthermore, both ends of each of the slide shafts 22a and 22b are fixed to the frame (see FIGS. 7A to 7C) of the analyzer 30.

The main slider 11 includes a main body 12 and shaft-receiving parts 13a and 13b. The shaft-receiving parts 13a and 13b are provided for the main body 12 and are disposed at a certain interval in the sliding direction. The shaft-receiving parts 13a and 13b each have two shaft holes 14 formed to allow both the slide shafts 22a and 22b that are disposed in parallel with each other to be inserted therethrough (see FIGS. 5 and 6).

This configuration allows the main slider 11 to slide along the slide shafts 22a and 22b. In this embodiment, the main body 12 and the shaft-receiving parts 13a and 13b are formed integrally but are not limited thereto.

Furthermore, the main slider 11 is joined to the tray 1 by a portion of the tray 1 located on the second position side. The main slider 11 and the tray 1 are joined to each other in such a manner that the tray 1 swings around the shaft perpendicular to two directions, the direction in which the tray 1 slides and the normal direction of the analysis tool 40 (see FIG. 1) placed on the tray 1.

Specifically, a shaft hole 6 is provided perpendicularly to the above-mentioned two directions in a portion of the tray 1 located on the second position side. The main body 12 of the main slider 11 is provided with a shaft 15 in such a manner that it is perpendicular to the slide shafts 22a and 22b. When the shaft 15 of the main slider 11 is inserted into the shaft hole 6 of the tray 1, the tray 1 is able to swing around the shaft 15 of the main slider 11 (see FIGS. 5 and 6). Moreover, when the main slider 11 is allowed to slide, the tray 1 also moves thereby (see FIGS. 5 and 6).

The subslider 16 includes wall parts 17a and 17b as well as a shaft-receiving part 20. Like the shaft-receiving parts 13a and 13b of the main slider 11, as shown in FIGS. 4A and 4B, the shaft-receiving part 20 is provided with two shaft holes 21 that allow the slide shafts 22a and 22b (FIG. 3) that are disposed in parallel with each other to be inserted therethrough.

This configuration also allows the subslider 16 to slide along the slide shafts 22a and 22b as in the case of the main slider 11. However, as shown in FIGS. 5 and 6, the slide shafts 22a and 22b are inserted through the shaft-receiving part 20 of the subslider 16, with the shaft-receiving part 20 being located between the shaft-receiving parts 13a and 13b of the main slider 11. The movable range of the subslider 16 is limited by the shaft-receiving parts 13a and 13b.

The wall parts 17a and 17b are attached to the shaft-receiving part 20, with a distance being provided between the wall parts 17a and 17b and the respective wall surfaces thereof being parallel to the slide shafts 22a and 22b. The portion of the wall part 17a located away from the shaft-receiving part 20 has a shape projecting toward the wall part 17b. This portion is in contact with the wall part 17b and thereby the distance between the wall parts 17a and 17b is kept constant.

A groove 18 is formed in the wall part 17a and a groove 19 is formed in the wall part 17b. Each of the groove 18 and the groove 19 is configured with an upper groove and a lower groove being connected to each other with an inclined groove. In other words, the grooves 18 and 19 each do not have a linear shape but a stepped shape. However, the groove 18 and the groove 19 are not identical in shape and are different from each other in terms of the position of the inclined groove.

Like the main slider 11, the subslider 16 also is joined to the tray 1. However, the subslider 16 is joined to the tray 1 through a cam mechanism, which is different from the main slider 11. Specifically, the cam mechanism is composed of the shaft 7 projected from the tray 1 and the groove 18 formed in the wall part 17a of the subslider 16. The shaft 7 of the tray 1 is inserted into the groove 18 as shown in FIG. 5.

With this configuration, when the subslider 16 is moved, the position of the shaft 7 in the vertical direction changes depending on the position of the subslider 16 and consequently, the tray 1 swings around the shaft 15 (see FIGS. 5 and 6). In other words, the shaft 7 functions as a cam follower and the groove 18 as a cam groove. The cam mechanism composed of the shaft 7 and the groove 18 swings the tray 1 around the shaft 15 depending on the position of the subslider 16.

As shown in FIG. 3, the analyzer of this embodiment further includes a connector 23 that is connected to the analysis tool 40 and a supporting part 29 that supports the analysis tool 40 through the open part 3 of the tray 1. When the tray 1 is located in the second position (see FIG. 6), the connector 23 is connected to the analysis tool 40 from the upper side of the analysis tool 40 placed on the tray 1, in the opposing position to the center of the arc thereof. When the tray 1 is located in the second position (see FIG. 6), the supporting part 29 supports the analysis tool 40 in the opposing position to the connector 23.

Specifically, the connector 23 has a plurality of connecting pins 24 on the leading end thereof. The connector 23 and the analysis tool 40 are connected together by inserting the connecting pins 24 into the connecting holes 48 of the transparent cover 42 (see FIG. 2). The connector 23 is held by an arm member 25 and is carried to the analysis tool 40.

The arm member 25 reciprocates the connector 23 between a position where the connector 23 is located away (in the upper direction) from the analysis tool 40 and a position where the connector 23 is connected to the analysis tool 40. As shown in FIG. 6, the arm member 25 can lower the connector 23 to allow the connector 23 to be connected to the analysis tool 40 when the tray 1 is located in the second position.

Specifically, the arm member 25 includes a C-shaped portion 26 and is joined to the connector 23 by two end portions 25a and 25b that constitute "C", with the connector 23 being rotatable with respect to the end portions 25a and 25b. Furthermore, the arm member 25 is attached to the frame (see FIGS. 7A, 7B and 7C) of the analyzer 30 by the opposing portion to the C-shaped portion 26. The arm member 25 is attached to the analyzer by inserting a projection provided for the frame (see FIGS. 7A, 7B and 7C) into a mounting hole 27. The arm member 25 is rotatable around the shaft that passes through the mounting hole 27.

The arm member 25 also is joined to the subslider 16 through the cam mechanism as in the case of the tray 1. The cam mechanism for joining the arm member 25 to the subslider 16 is composed of a shaft 28 provided for the arm member 25 and a groove 19 formed in the wall part 17b of the subslider 16. As shown in FIGS. 5 and 6, this shaft 28 is inserted into the groove 19 in parallel with the shaft 7 of the tray 1.

With this configuration, when the subslider 16 is moved, the position of the shaft 28 in the vertical direction also changes depending on the position of the subslider 16 as in the case of the shaft 7. In other words, the shaft 28 functions as a cam follower and the groove 19 as a cam groove. Consequently, the arm member 25 swings around the mounting hole 27 (see FIGS. 5 and 6).

The groove 19 is formed so that the arm member 25 moves downwards when the subslider 16 is moved backwards (i.e. when the subslider 16 is moved in the direction in which the shaft-receiving part 20 of the subslider 16 approaches the shaft-receiving part 13b of the main slider 11). Therefore, as shown in FIG. 6, when the tray 1 is located in the second position, i.e. when optical measurement is performed, the analysis tool 40 and the connector 23 are connected together. In this stage, the analysis tool 40 is sandwiched between the connector 23 and the supporting part 29 and thereby the analysis tool 40 is positioned reliably.

In this embodiment, the connector 23 includes a rotator 23a and a holder 23b that holds the rotator 23a, with the rotator 23a being rotatable. The connecting pins 24 are provided for the rotator 23a. On the other hand, the holder 23b is joined to the end portions 25a and 25b of the arm member 25.

Accordingly, in this embodiment, when the connector 23 is connected to the analysis tool 40, the rotator 23a is rotated around the long axis thereof and thereby the analysis tool 40 can be rotated. When a configuration is employed in which, for example, a servomotor rotates the rotator 23a in conjunction with optical measurement, the cells 44 subjected to the optical measurement (see FIG. 2) can be changed sequentially.

However, even if the analysis tool 40 is intended to be rotated by the rotator 23a, the analysis tool 40 is difficult to rotate when it is held by the holding sections 2 of the tray 1. Accordingly, in this embodiment, when (or after) the connector 23 is connected to the analysis tool 40, holding of the analysis tool 40 by the holding sections 2 of the tray 1 is released.

Specifically, the holding sections 2 each are composed of a positioning section 4 and a convex section 5. Therefore, when the portions where the holding sections 2 of the tray 1 are formed move downwards, with the vertical position of the analysis tool 40 being maintained by the supporting part 29, holding of the analysis tool 40 by the holding sections 2 is released. Therefore, the groove 18 is formed to swing the tray 1 downwards when the subslider 16 is moved backwards (i.e. when the subslider 16 is moved in the direction in which the shaft-receiving part 20 of the subslider 16 approaches the shaft-receiving part 13b of the main slider 11).

That is, in this embodiment, when the subslider 16 is moved backwards, with the tray being located in the second position, the connector 23 is connected to the analysis tool 40 and thereby holding of the analysis tool 40 by the holding sections 2 of the tray 1 is released. Accordingly, accurate positioning of the analysis tool 40 and efficient optical measurement through rotation of the analysis tool 40 are achieved. Moreover, since the analysis tool 40 is not inserted directly into the inner part by a user, unlike the conventional cases, the analysis tool 40 itself does not slide. Thus, this embodiment can prevent dust and dirt from entering as compared to conventional cases.

However, this embodiment is not limited to the example described above. For example, a mode also can be employed in which the connector 23 and the arm member are located under the tray 1 and the supporting part 29 is located above the tray 1. Similarly in this mode, the analysis tool 40 is sandwiched between the connector 23 and the supporting part 29 and thereby the analysis tool 40 is positioned reliably. Moreover, this can prevent dust and dirt from entering as compared to conventional cases.

Figure 7A:
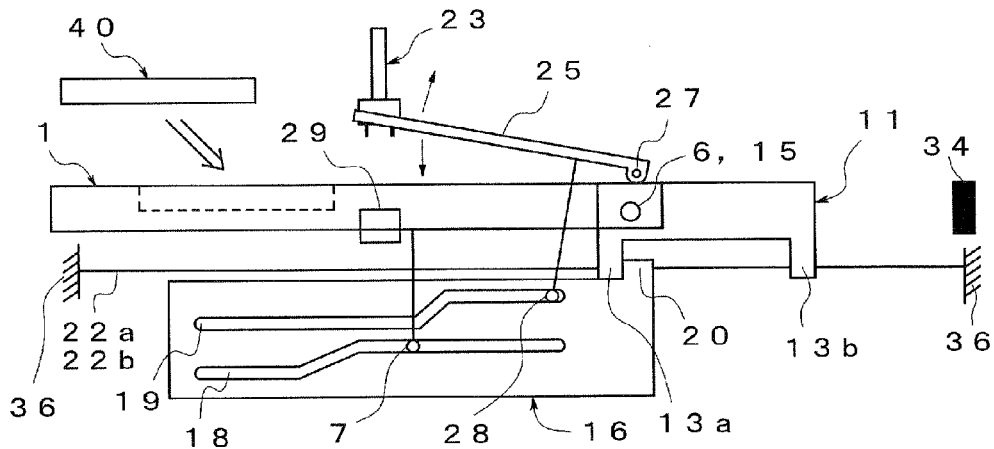
FIGS. 7A to 7C schematically show a series of operations of the analyzer according to the embodiment.
Figure 7B:
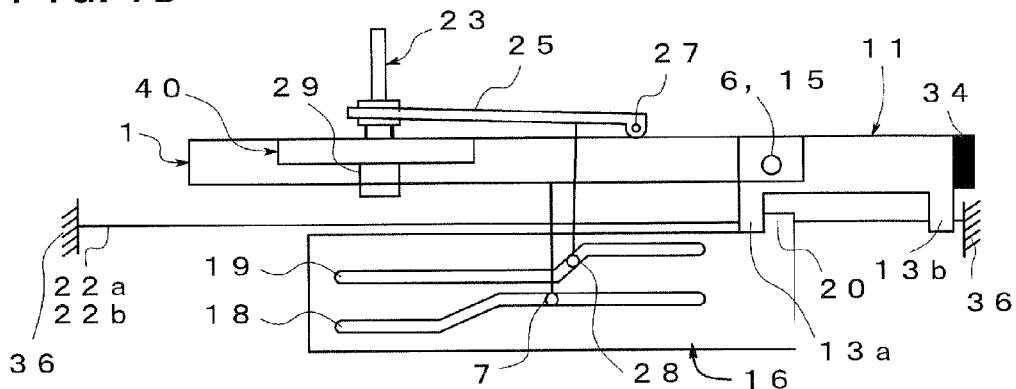
Figure 7C:
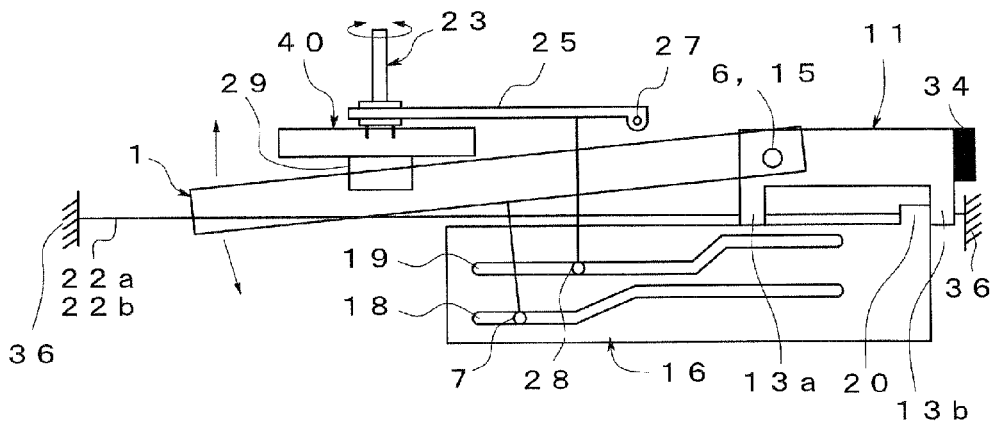

Operations of the tray 1 and the arm member 25 are described with reference to FIGS. 7A to 7C. FIGS. 7A to 7C schematically show a series of operations of the analyzer according to this embodiment. In FIGS. 7A to 7C, each structural member is represented with a simplified model. Furthermore, the following description is made also with suitable reference to FIGS. 3 to 6.

First, FIG. 7A is described. FIG. 7A schematically shows the state shown in FIG. 5. In the state shown in FIG. 7A, the main slider 11 has been moved to the front side (the outer side of the analyzer 30) and the tray 1 also has been moved to the front side accordingly. The tray 1 is located in the first position where the analysis tool 40 placed thereon is exposed to the outside of the analyzer 30.

In the state shown in FIG. 7A, the analysis tool 40 is placed on the tray 1. Although it is not shown in FIGS. 7A to 7C, the position of the main slider 11 on the front side (ejected position) is determined by the positioning member (see FIGS. 8A and 8B) attached to the frame 36.

Furthermore, in the state shown in FIG. 7A, the subslider 16 has moved to the front side until the shaft-receiving part 20 thereof comes into contact with the shaft-receiving part 13a of the main slider 11 located on the front side. In this stage, the shaft 7 of the tray 1 is located in the upper stage of the groove 18 and the tray 1 is horizontal. On the other hand, the shaft 28 of the arm member 25 is located in the upper stage of the groove 19, but the arm member 25 is not horizontal and the position of the C-shaped portion 26 (see FIG. 3) thereof rises. The connector 23 is located on the upper side of the analysis tool 40 placed on the tray 1.

Subsequently, as shown in FIG. 7B, when the main slider 11 moves to the back side (to the inner side of the analyzer 30) from the state shown in FIG. 7A, the tray 1 and the subslider 16 also moves to the back side together with the main slider 11. In this stage, the position (retracted position) of the main slider 11 located on the back side is determined by a positioning member 34 attached to the frame 36. In this embodiment, the position of the tray 1 where the main slider 11 is in contact with the positioning member 34 is referred to as the second position.

Furthermore, in the state shown in FIG. 7B, the positional relationship between the tray 1 and the subslider 16 remains unchanged. Accordingly, the positional relationship between the shaft 7 and the groove 18 also remains unchanged and the tray 1 stays horizontal. On the other hand, as described above, the arm member 25 is attached to the frame 36 and does not move together with the main slider 11. Therefore, the positional relationship between the arm member 25 and the subslider 16 changes and the relative position of the shaft 28 inside the groove 19 also changes. Specifically, as shown in FIG. 7B, since the shaft 28 of the arm member 25 moves downwards along the groove 19, the position of the C-shaped portion 26 (see FIG. 3) of the arm member 25 is lowered. The connector 23 approaches the analysis tool 40 placed on the tray 1.

Subsequently, in the state shown in FIG. 7C, that is, as shown in FIG. 6, when the subslider 16 alone moves to the back side, the shaft 28 of the arm member 25 moves to the lower stage of the groove 19 and the connector 23 is connected to the analysis tool 40. Furthermore, the shaft 7 of the tray 1 moves to the lower stage of the groove 18 after the shaft 28 has moved completely to the lower stage of the groove 19. The tray 1 swings and the holding sections 2 thereof moves downwards, and thereby holding of the analysis tool 40 held by the holding sections 2 is released. The analysis tool 40 is then sandwiched between the connector 23 and the supporting part 29 and the connector 23 allows the analysis tool 40 to be rotatable. In this state, optical measurement is performed.

In this embodiment, the cam mechanism that joins the subslider 16 and the tray 1 together allows the connector 23 attached to the arm member 25 to be connected to the analysis tool 40 before the holding sections 2 of the tray 1 are moved downwards. However, the cam mechanism is not limited thereto. This embodiment may employ a mode in which the cam mechanism that joins the subslider 16 and the tray 1 together allows the connector 23 to be connected to the analysis tool 40 at the same time the holding sections 2 are moved downwards.

As described above, the drive mechanism 10 shown in FIGS. 3 to 7C makes it possible to achieve operations by only sliding movements of the main slider 11 and the subslider 16. The operations include retraction and ejection of the tray 1, holding of the analysis tool 40 by the tray 1 and release thereof, and connecting of the connector 23 and release thereof. Furthermore, the directions of the sliding movements are the same. Therefore, as described later, the configuration of a mechanism (power transmission mechanism) for power transmission can be simplified. Moreover, since the operation timing between respective operations also can be determined without using a sensor or a controller, the cost of the analyzer 30 can be prevented from increasing.

In FIGS. 3 to 7C, although it is not shown, the main slider 11 and the subslider 16 are moved by power transmitted from a power source inside the analyzer 30. In this embodiment, the mechanism for power transmission (power transmission mechanism) is not particularly limited. Examples thereof include one shown in FIGS. 8A and 8B.

An example of the power transmission mechanism employed in this embodiment is described with reference to FIGS. 8A and 8B. FIGS. 8A and 8B are diagrams showing an example of the power transmission mechanism of this embodiment. FIG. 8A shows the state where the tray is located inside the analyzer. FIG. 8B shows the state where the tray is located outside the analyzer.

In the example shown in FIGS. 8A and 8B, an electric motor 55 is used as the power source. Power of the electric motor 55 is transmitted to the main slider 11 and the subslider 16 through the belt 53. Specifically, as shown in FIGS. 8A and 8B, the subslider 16 is fixed to the belt 53 by the shaft-receiving part 20. When the output shaft of the electric motor 55 is rotated to move the belt 53, the subslider 16 moves accordingly. In FIGS. 8A and 8B, numerals 56, 57, 58, and 59 indicate pulleys.

On the other hand, since the main slider 11 is not fixed to the belt 53, it does not always move to follow the movement of the belt 53. Instead, however, the main slider 11 is provided with a projection 52 that can project and that can be retracted, on the lower side (upper side on the paper in FIGS. 8A and 8B) of the shaft-receiving part 13b. Furthermore, the main slider 11 also is provided with a pin 51 that can project and that can be retracted, on the back side of the shaft-receiving part 13b.

This pin 51 and the projection 52 move in conjunction with each other. As shown in FIG. 8B, when the pin 51 projects, the projection 52 also projects. On the other hand, as shown in FIG. 8A, when the main slider 11 is in contact with the positioning member 34 and thereby the pin 51 is retracted, the projection 52 also is retracted (the retracted state is indicated with a broken line).

The projection 52 can be caught by a projected catching part 54 provided on the belt 53. When the projection 52 is caught by the catching part 54 by the portion located on the opposite side to the direction in which the belt 53 moves and is pushed thereby, the main slider 11 is moved by the belt 53.

Now, consideration is given to the case where the ejected tray 1 is retracted into the analyzer 30 (see FIG. 5). In the case where the state shown in FIG. 7A is changed to the state shown in FIG. 7B, the pin 51 is not retracted and the projection 52 projects as shown in FIG. 8B. Furthermore, the catching part 54 is provided on the belt 53 so as to be in contact with the front side (lower side in FIGS. 8A and B) of the projection 52 when the shaft-receiving part 20 of the subslider 11 is in contact with the shaft-receiving part 13a located on the front side of the main slider.

Therefore, as shown in FIG. 8B, the projection 52 is caught by the catching part 54 by its front side in the state shown in FIG. 7A. Accordingly, when the electric motor 53 rotates the pulley 56 clockwise, the main slider 11 is moved to the back side (upper side in FIGS. 8A and 8B) by the belt 53. In this case, the subslider 16 also moves to the back side together.

When the main slider 11 comes into contact with the positioning member 34 (the state shown in FIG. 7B), the pin 51 is retracted and thereby the projection 52 also is retracted. In this case, the belt 53 further can move. Accordingly, as shown in FIG. 8A, only the subslider 16 (shaft-receiving part 20) is moved to a further back side by the belt 53 (see FIGS. 5 and 7C).

Next, consideration is given to the case where the retracted tray 1 is ejected and the analysis tool 40 is then removed. First, in the case where the state shown in FIG. 7C is changed to the state shown in FIG. 7B, the electric motor 55 transmits power to the pulley 56 and thereby the belt 53 moves counterclockwise. Accordingly, as shown in FIG. 8A, the subslider 16 moves to the front side (lower side in FIGS. 8A and 8B) and the shaft-receiving part 20 thereof comes into contact with the shaft-receiving part 13a of the main slider 11.

Furthermore, when the belt 53 moves further, the main slider 11 moves to the front side while being pushed by the subslider 16, until it comes to contact with the positioning member 35. Moreover, when the shaft-receiving part 13b of the main slider 11 moves away from the positioning member 34, the pin 51 is projected and thereby the projection 52 projects (see FIG. 8B).

As described above, the use of the power transmission mechanism shown in FIGS. 8A and 8B makes it possible to retract and eject the tray 1, to hold the analysis tool 40 using the tray 1 and release it, and to connect the connector 23 and release it by merely rotating the power shaft of the electric motor 55 either clockwise or counterclockwise. In this case, it is not necessary to control the electric motor 55 with high precision and to use a sensor for position detection. Accordingly, the use of the power transmission mechanism shown in FIGS. 8A and 8B allows a stepping motor with a coarse step angle or an inexpensive DC motor to be used as the electric motor 55. Thus the cost of the analyzer 30 can be reduced.

As described above, the present invention is useful for an analyzer in which an analysis tool is used to perform optical measurement with respect to a sample. Thus, the analyzer of the present invention has industrial applicability.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:
1. An analyzer in which optical measurement is performed with respect to a sample placed in a cell of an analysis tool, comprising:
  a light source unit that emits light for optical measurement;
  a light-receiving unit that receives light emitted from the light source unit and transmitted through the sample or reflected by the sample;
  a tray on which the analysis tool is placed, wherein the tray has an open part in a portion where the analysis tool is placed; and
  a drive mechanism for driving the tray, the tray comprises a holding section that holds, in a predetermined position, the analysis tool placed on the tray, the drive mechanism reciprocates the tray between a first position where the analysis tool placed on the tray is exposed to the outside of the analyzer and a second position where the analysis tool placed on the tray is accommodated inside the analyzer, the light source unit is disposed so that emitted light is incident on the cell of the analysis tool when the tray is located in the second position, and the light- receiving unit is disposed so as to receive light transmitted through the cell when the tray is located in the second position;

the analyzer further comprises a connector connected to the analysis tool and a supporting part supporting the analysis tool through the open part, wherein the connector is connected to the analysis tool when the tray is located in the second position, the supporting part supports the analysis tool in an opposite position to the connector, and completion of connection by the connector and support by the supporting part releases holding of the analysis tool by the holding section.

2. The analyzer according to claim 1, wherein all or part of a side wall of the open part is formed to conform to an outer shape of the analysis tool, the side wall of the open part has a convex section formed thereon that projects toward the inner side of the open part, and a portion formed to conform to the outer shape of the analysis tool and the convex section function as the holding section.

3. The analyzer according to claim 1, wherein the drive mechanism comprises a first slider and a second slider that slide along a direction in which the tray reciprocates, the first slider is joined to a portion of the tray located on a side of the second position so that the tray swings around a shaft perpendicular to a direction in which the tray slides and a normal direction of the analysis tool placed thereon, the second slider is joined to the tray through a cam mechanism, the cam mechanism is configured so that the tray swings around the shaft depending on the position of the second slider, and holding of the analysis tool by the holding section is released when the tray is swung by the cam mechanism to move the holding section of the tray.

4. The analyzer according to claim 3, wherein the analyzer further comprises an arm member for joining the connector and the second slider to each other, and the arm member reciprocates the connector between a position where the connector is located away from the analysis tool and a position where it is connected to the analysis tool depending on the position of the second slider, and the connector is connected to the analysis tool after or before the cam mechanism moves the holding section of the tray.

* * * * *